United States Patent
Kladders et al.

[11] Patent Number: 5,833,088
[45] Date of Patent: Nov. 10, 1998

[54] CONTAINER WITH CLOSURE CAP AND METHOD OF FILLING CONTAINERS WITHOUT GAS BUBBLES

[75] Inventors: Heinrich Kladders, Mülheim; Bernhard Freund, Gau-Algesheim; Wulf Bachtler, Mainz; Joachim Jaeger, Bruchsal; Joachim Eicher, Dortmund, all of Germany

[73] Assignee: Boehringer Ingelheim KG, Ingelheim am Rhein, Germany

[21] Appl. No.: 776,864

[22] PCT Filed: Aug. 11, 1995

[86] PCT No.: PCT/EP95/03183

§ 371 Date: Jul. 14, 1997

§ 102(e) Date: Jul. 14, 1997

[87] PCT Pub. No.: WO96/06011

PCT Pub. Date: Feb. 29, 1996

[30] Foreign Application Priority Data

Aug. 11, 1994 [DE] Germany .......................... 44 28 434.9

[51] Int. Cl.⁶ .................................................. B65D 51/16
[52] U.S. Cl. .......................... 215/248; 215/307; 215/354; 220/366.1; 220/785
[58] Field of Search .............................. 220/366.1, 367.1, 220/799, 796, 800–804, 806, 780, 784, 785, 788, 792, 795, 360, 361, 363, 369, 373; 215/231, 320, 317, 354, 307, 310, 247, 248, 352

[56] References Cited

U.S. PATENT DOCUMENTS

| | | |
|---|---|---|
| 1,694,851 | 12/1928 | Glass . |
| 2,424,801 | 7/1947 | Crabbe et al. . |
| 2,629,421 | 2/1953 | Ayres ................................ 220/366.1 X |
| 2,669,370 | 2/1954 | Royall . |
| 2,990,079 | 6/1961 | Garvey ............................. 220/366.1 X |
| 3,193,993 | 7/1965 | Barton et al. . |
| 4,008,820 | 2/1977 | Ruetz . |
| 4,187,893 | 2/1980 | Bujan . |
| 4,202,334 | 5/1980 | Elson ................................ 220/366.1 X |
| 4,204,606 | 5/1980 | Micheli ..................................... 215/307 |
| 4,799,599 | 1/1989 | Herrmann ................................ 215/307 |
| 4,883,641 | 11/1989 | Wicks et al. ......................... 215/355 X |
| 4,886,177 | 12/1989 | Foster . |
| 5,038,958 | 8/1991 | Dreir .................................... 220/366.1 |
| 5,084,042 | 1/1992 | McPhee . |
| 5,325,977 | 7/1994 | Haynes et al. . |
| 5,455,124 | 10/1995 | Schollenberger ................... 220/361 X |
| 5,509,564 | 4/1996 | Knoop .............................. 220/367.1 X |
| 5,672,321 | 9/1997 | Daykin ................................ 215/354 X |

FOREIGN PATENT DOCUMENTS

| | | |
|---|---|---|
| 0 217 425 | 4/1987 | European Pat. Off. . |
| 0 532 873 | 3/1993 | European Pat. Off. . |
| 780 143 | 4/1935 | France . |
| 1159909 | 7/1958 | France . |
| 2847929 | 5/1980 | Germany ............................ 220/366.1 |
| 449648 | 12/1949 | Italy ....................................... 220/231 |
| 90/0626 | 6/1990 | WIPO . |

*Primary Examiner*—Stephen K. Cronin
*Assistant Examiner*—Nathan Newhouse
*Attorney, Agent, or Firm*—Robert P. Raymond; Alan R. Stempel; Mary-Ellen Devlin

[57] ABSTRACT

A closure cap for sealing containers without gas bubbles displaces some of the contents of the container when fitted onto the neck of the container and at the same time allows any trapped gas to escape through one or more vents before the closure cap engages in the closure position.

9 Claims, 3 Drawing Sheets

CONTAINER WITH CLOSURE CAP AND METHOD OF FILLING CONTAINERS WITHOUT GAS BUBBLES

The invention relates to a container with closure cap for filling with liquids without gas bubbles. The invention relates in particular to a closure cap by means of which containers can be filled with liquids without gas bubbles.

For numerous applications it is necessary to transfer liquids into containers in such a way that no residual air or gas is included. Such a requirement applies, for example, to containers for pharmaceutical solutions which are used in certain inhalers which meter liquids by means of a measuring chamber (cf. for example WO 91/14468, see FIG. 1). Since the liquid to be metered in this case frequently contains highly effective pharmaceutical substances which have to be accurately metered, the range of fluctuations in the dosage administered must be as small as possible; otherwise, the patient will not receive the quantity of active substance prescribed by the doctor. In view of the tiny amount of liquid administered per dose, even relatively small bubbles lead to high percentage deviations in the above-mentioned inhalers.

The invention now relates to a container and more particularly to a closure cap and a process for filling containers without gas bubbles. The closure cap is constructed so that, when placed on the neck of the container, it displaces some of the contents of the container and at the same time allows any gas enclosed therein to escape and engages in the closure position. The closure may contain means for guiding a cannula for removing liquid from the container.

Figure 1:
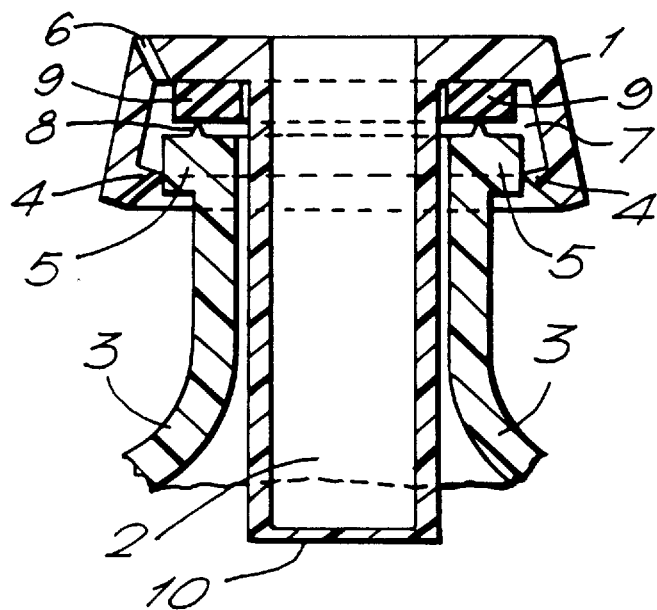
FIG. 1 shows an axial section through the centre of a closure cap of this kind.

In FIG. 1, the flexible closure cap (1) has a device (2)—in this case in the form of a dipping nozzle—through which some of the contents of the container (3) are displaced during the closure process. An inner encircling bead (4) (crimped edge) on the lower rim of the closure cap (1) engages in the closure position below a cylindrical ring (5) running around the outside of the neck of the container. Whilst the closure cap (1) is being pushed on, the rim of the closure cap expands and the bead (4) abuts on the ring (5) to form a seal, so that the only communication between the interior (7) of the cap and the exterior is through one or more vents (6). In the closure position the gap between the flat part of the closure cap (1) and the upper edge of the neck of the container, which may optionally be provided with an encircling rib (8) to improve the seal, is filled by a sealing ring (9) and in this way the interior of the container (3) is reliably sealed off from the interior (7) of the cap, which surrounds the sealing ring (9) and the neck of the container (3). The internal diameter of the sealing ring (9) is preferably selected so that it fits tightly against the device (2). The vent or vents (6) may also be located at other points on the exterior of the cap, possibly on the side, in the cylindrical part of the cap.

Figure 2:
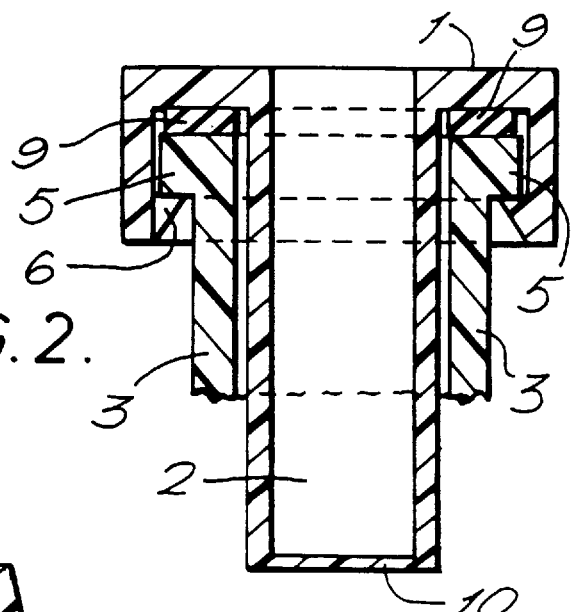
FIG. 2 shows, again in axial section, the neck of a container with the closure cap according to the invention fitted thereon in the closure position, the vents being arranged differently.

FIG. 2 shows the neck of the container with the closure cap (1) fitted thereon in the closure position. However, in this case, venting is achieved by the fact that vents (6) in the form of recesses are provided in the encircling bead (4) of the closure cap (1). Alternatively, recesses in the ring (5) may also serve as venting means (see FIG. 3). The dipping nozzle (2) is sealed off by a membrane (10) at the lower end. In order to remove liquid, the membrane is pierced with a cannula.

Figure 3:
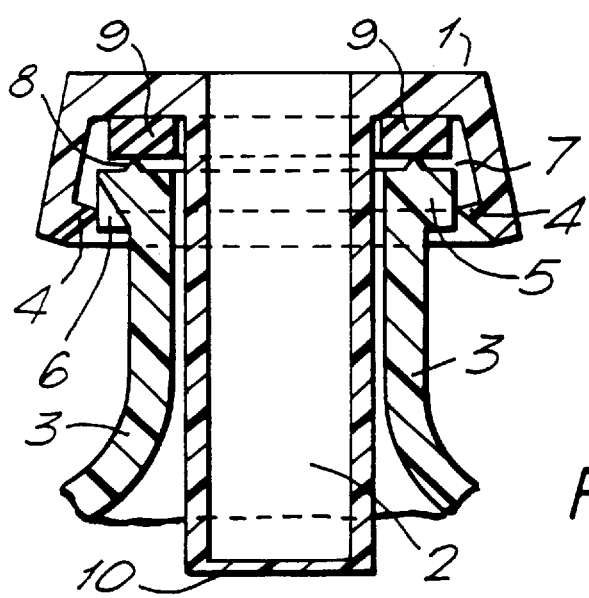
FIG. 3 shows the embodiment according to the invention, wherein the vents (at least one) are provided in the form of recesses on the upper part of the container.
Figure 3A:
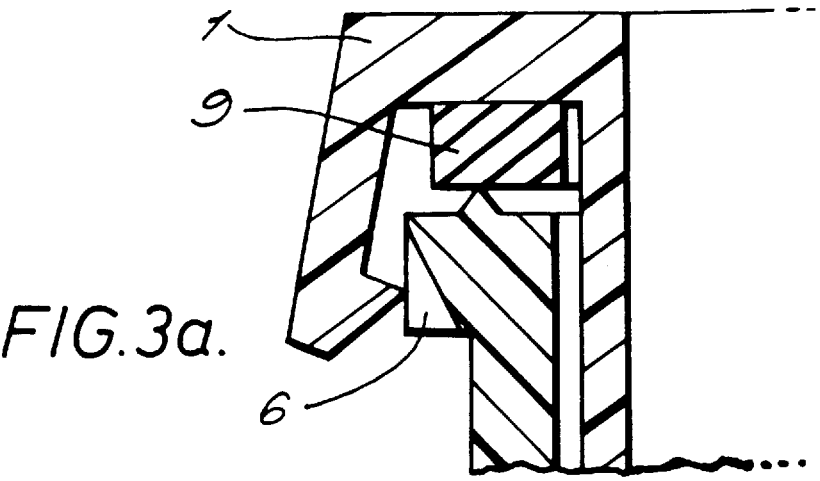
FIG. 3a shows an enlarged view of the embodiment according to the invention.

FIG. 3 shows, again in axial section, the neck of a container with the closure cap fitted thereon during the closing process. As shown in FIG. 3, there is at least one vent (6) in the ring (5) of the container. Preferably, the vents are arranged in the form of recesses in the ring (5). Alternatively, the vents may be provided in the form of bores. The vents (6) are arranged in such a way that the air can escape from the interior (7) of the cap during the closure process through the vents (6), but after the container has been sealed there is no longer any communication between the liquid inside the container and the vents.

Figure 4:
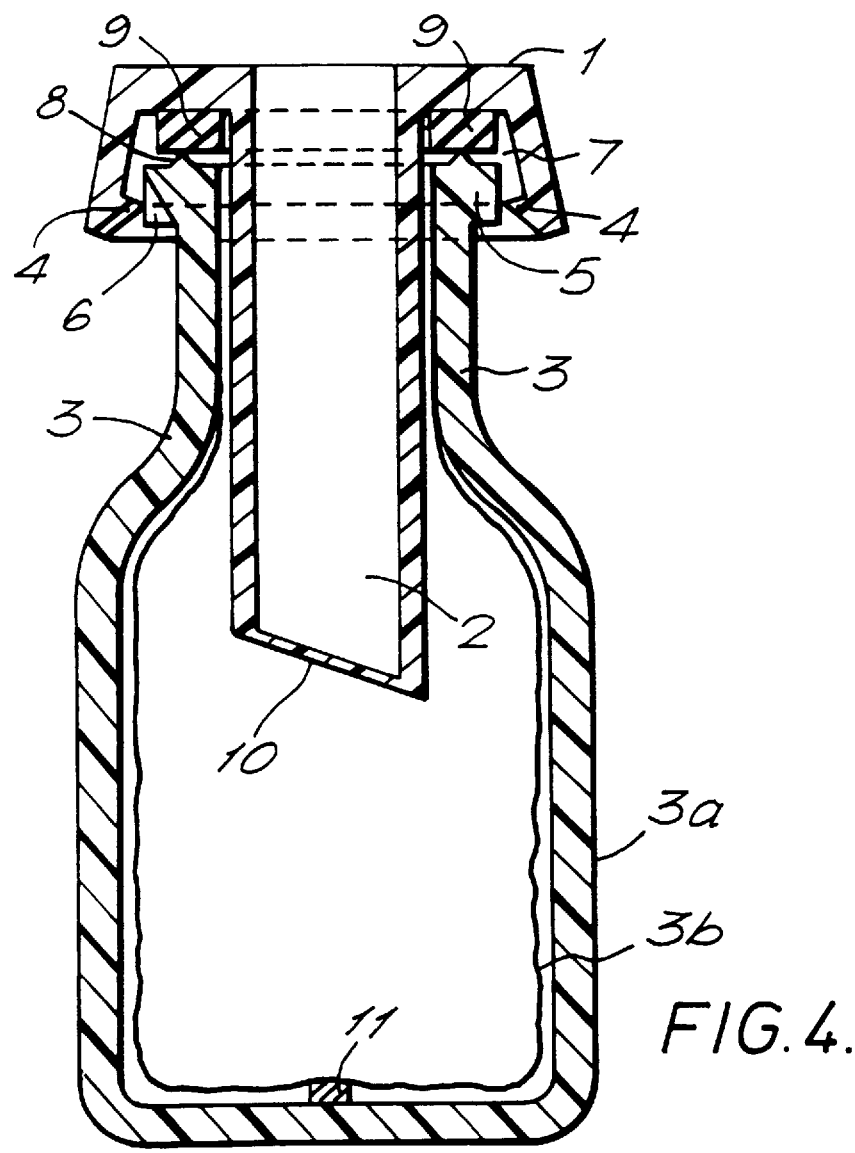
FIG. 4 shows the container according to the invention with the closure cap fitted thereon.

FIG. 4 shows, in axial section, a container according to the invention with a closure cap fitted thereon, the vent or vents being provided in the outer part of the ring (5). The vents may be provided in the form of recesses.

In a preferred embodiment, the container (3) consists of a dimensionally stable outer container and a readily deformable inner bag (3b) which collapses onto itself as the liquid is removed. In these embodiments, any residual air bubbles would be particularly detrimental. Such containers are described, for example, in European Patent 532873, the contents of which are hereby referred to. The device (11) serves to secure the deformable inner bag (3b) to the inner wall of the fixed external container (3a) facing the bag (3b).

Figure 5A:
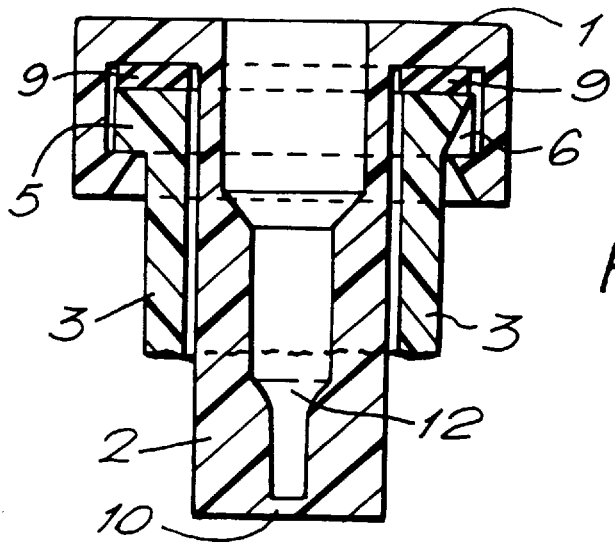
FIG. 5 shows a closure cap according to the invention with guide means for the cannula for removing the liquid.

FIG. 5a shows a preferred embodiment of the closure cap according to the invention, in which the interior of the dipping nozzle is constructed so as to form a guide (12) for a cannula for the removal of liquid. In the present instance the vents (6) are provided on the upper part of the container (3). As already described, the vents may alternatively be provided on the closure cap.

Figure 5B:
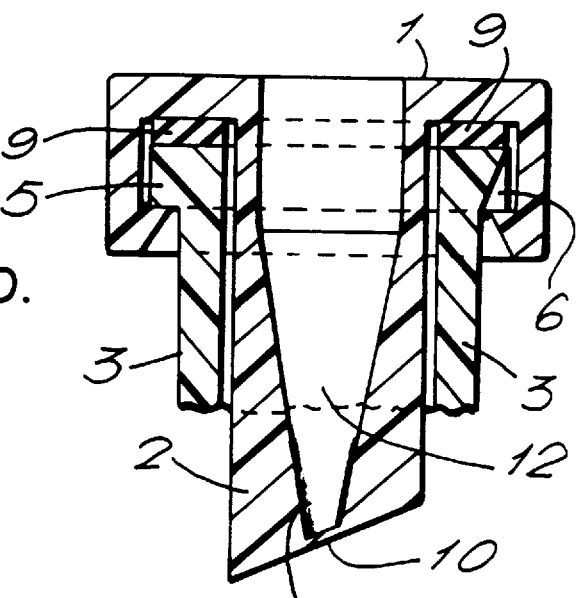
Figure 5C:
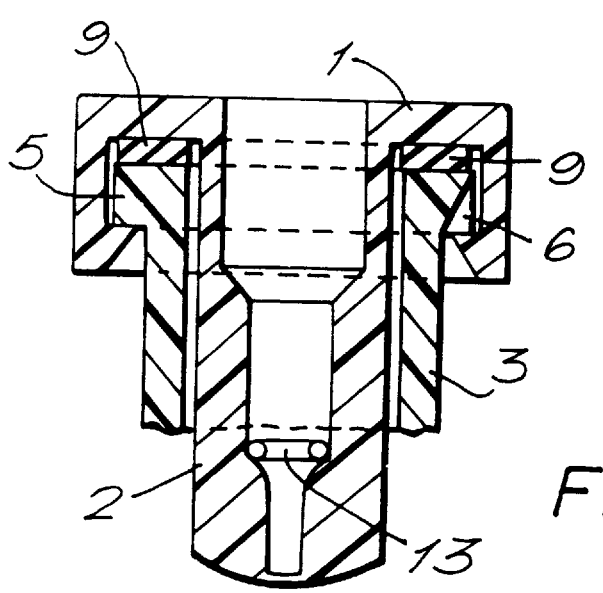

FIGS. 5b and 5c show other embodiments with regard to the construction of the dipping nozzle (2) and the guide (12) for the cannula for removing liquid.

FIG. 5b shows an embodiment in which the guide (12) merges into a press fit (14). The press fit is designed, in terms of diameter and length, so that on the one hand the resistance to the insertion of the cannula is minimised and on the other hand an adequate seal is achieved between the nozzle and cannula.

FIG. 5c shows an embodiment having a flexible O-ring seal (13) between the nozzle and the inserted cannula, in which the cannula is not shown.

As shown in FIGS. 5b and 5c, the lower end of the dipping nozzle with the membrane (10) may preferably be chamfered, preferably by 40° to 70° relative to the nozzle axis. This makes it easier for the membrane to be pierced by a "blunt" cannula the end face of which is perpendicular to the axis of the cannula. The advantages of a blunt as opposed to a sharpened cannula are the lower risk of injury to the user, the reduced labour involved in producing the end face of the cannula and the reduced risk of particle abrasion on the nozzle wall when the cannula is inserted.

The drawings show a sealing ring (9) and an encircling rib (8). In an alternative embodiment the encircling rib (8) may be omitted if all the parts are manufactured with high precision to fit exactly.

In order to remove liquid from the container (3) the membrane (10) is pierced with a cannula. The preferred embodiments are those wherein the container (3) has a readily deformable inner bag (3b) and the tip of the cannula is located half way up the container when the liquid is removed. In this case, air bubbles are least problematic.

The container and closure cap (1) are generally made of plastics material. Since the liquid transferred into the container is not compressible in practice, the system comprising the container and closure cap must be sufficiently deformable to allow expansion of the liquid in heat. Similarly, when the liquid is removed the walls of the container must be capable of yielding sufficiently or collapsing. Suitable plastics, consisting of polyethylene or polypropylene, for example, are available to those skilled in the art for the manufacture of these containers and for the closure cap (1).

We claim:

1. An assembly for holding a liquid, said assembly comprising:
   (a) a container (3) having an inside and an outside, and a neck defining a passage through which liquid may be introduced into the side of the container;
   (b) a closure cap (1) for sealing the container, said closure cap comprising,
      (1) a dipping nozzle (2) which displaces part of the contents of the container when the closure cap is pushed onto the neck of the container, said dipping nozzle having an interior which forms a guide (12) that runs along an axis of said nozzle, said guide having a first end that is open and a second, closed, end that is terminated with a membrane (10) that is adopted to be pierced by a cannula which has been inserted into said guide, and
      (2) one or more vents (6) for establishing communication between the inside and the outside of the container, as the container is closed with the closure cap, to thereby allow gas and/or liquid displaced by the dipping nozzle (2) to escape from the interior of the container.

2. An assembly in accordance with claim 1, further comprising means for forming a seal between said dipping nozzle and a cannula inserted into the guide, wherein the means for forming a seal between said dipping nozzle and a cannula inserted into the guide is a rubber o-ring.

3. An assembly in accordance with claim 1, further comprising means for forming a seal between said dipping nozzle and a cannula inserted into the guide, wherein the means for forming a seal between said dipping nozzle and a cannula inserted into the guide is a portion of the guide of reduced diameter forming a press fit (14).

4. An assembly in accordance with claim 1, wherein the end of the dipping nozzle terminated by said membrane that is chamfered by placement of said membrane at an angle between 40° and 70° relative to the axis of said nozzle.

5. An assembly in accordance with claim 1, wherein a lower rim of the closure cap comprises an encircling bead (4) and wherein the neck of said container comprises a cylindrical ring (5), said elements being configured so that, when said closure cap is pushed onto said container, said lower rim of said cap expands and the bead (4) forms a seal against said ring (5).

6. An assembly in accordance with claim 5, wherein each vent (6) is a recess in the bead (4).

7. An assembly in accordance with claim 6, wherein each of said vents is so positioned with respect to the seal formed between said bead (4) and said ring (5) that, after the container has been closed, there is no longer any communication between the inside and the outside of said container.

8. An assembly in accordance with claim 1, wherein there is a readily deformable inner bag (3) within said container which is adapted to contain the liquid to be held within the assembly and which is adapted to collapse upon itself as liquid is withdrawn from the assembly.

9. An assembly for holding a liquid, said assembly comprising:
   (a) a container (3) having an inside and an outside, a neck defining a passage through which liquid may be introduced into inside of the container, wherein said neck comprises a cylindrical ring (5) and a readily deformable inner bag (3) within said container which is adapted to contain the liquid to be held within the assembly and which is adapted to collapse upon itself as liquid is withdrawn from the assembly;
   (b) a closure cap (1) for sealing the container, said closure cap comprising,
      (1) a dipping nozzle (2) which displaces part of the contents of the container when the closure cap is pushed onto the neck of the container, said dipping nozzle having an interior which forms a guide (12) that runs along an axis of said nozzle, said guide having a first end that is open and a second, closed, end that is terminated with a membrane (10) that is adopted to be pierced by a cannula which has been inserted into said guide, said guide (12) having means for forming a seal between said dipping nozzle and a cannula inserted into the guide, wherein the end of the dipping nozzle that is terminated by said membrane is chamfered by placement of said membrane at an angle between 40° and 70° relative to the axis of said nozzle,
      (2) a lower rim comprising an encircling bead (4) being so configured so that, when said closure cap is pushed onto said container, said lower rim of said cap expands and the bead (4) forms a seal against said ring (5),
      (3) one or more recesses in the bead (4) forming vents (6) for establishing communication between the inside and the outside of the container, as the container is closed with the closure cap, to thereby allow gas and/or liquid displaced by the dipping nozzle (2) to escape from the interior of the container, wherein each of said vents is so positioned with respect to the seal formed between said bead (4) and said ring (5) that, after the container has been closed, there is no longer any communication between the inside and the outside of said container.

* * * * *